(12) United States Patent
Ohban

(10) Patent No.: US 9,241,628 B2
(45) Date of Patent: Jan. 26, 2016

(54) OPHTHALMOLOGIC APPARATUS, METHOD FOR CONTROLLING OPHTHALMOLOGIC APPARATUS, AND PROGRAM

(71) Applicant: CANON KABUSHIKI KAISHA, Tokyo (JP)

(72) Inventor: Hideyuki Ohban, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/249,107

(22) Filed: Apr. 9, 2014

(65) Prior Publication Data
US 2014/0307228 A1   Oct. 16, 2014

(30) Foreign Application Priority Data
Apr. 12, 2013   (JP) ................. 2013-083947

(51) Int. Cl.
*A61B 3/14* (2006.01)
*A61B 3/15* (2006.01)
*A61B 3/12* (2006.01)

(52) U.S. Cl.
CPC .. *A61B 3/154* (2013.01); *A61B 3/12* (2013.01)

(58) Field of Classification Search
CPC ........ A61B 3/152; A61B 3/145; A61B 3/154; A61B 3/01; A61B 3/1522
USPC ................... 351/200, 205, 208, 246
See application file for complete search history.

(56) References Cited

U.S. PATENT DOCUMENTS 5,033,841 A * 7/1991 Nishio et al. ............. 351/212

FOREIGN PATENT DOCUMENTS

JP   06-046999 A   2/1994
JP   07-031590 A   2/1995

* cited by examiner

*Primary Examiner* — James Greece
(74) *Attorney, Agent, or Firm* — Canon U.S.A., Inc. IP Division

(57) ABSTRACT

An ophthalmologic apparatus is configured to determine a direction in which a target that is used to adjust a working distance comes into focus based on an influence of astigmatism contained in a cornea reflection image of an eye to be examined.

14 Claims, 12 Drawing Sheets

BLUR IN
LATERAL DIRECTION

BLUR IN
LONGITUDINAL DIRECTION

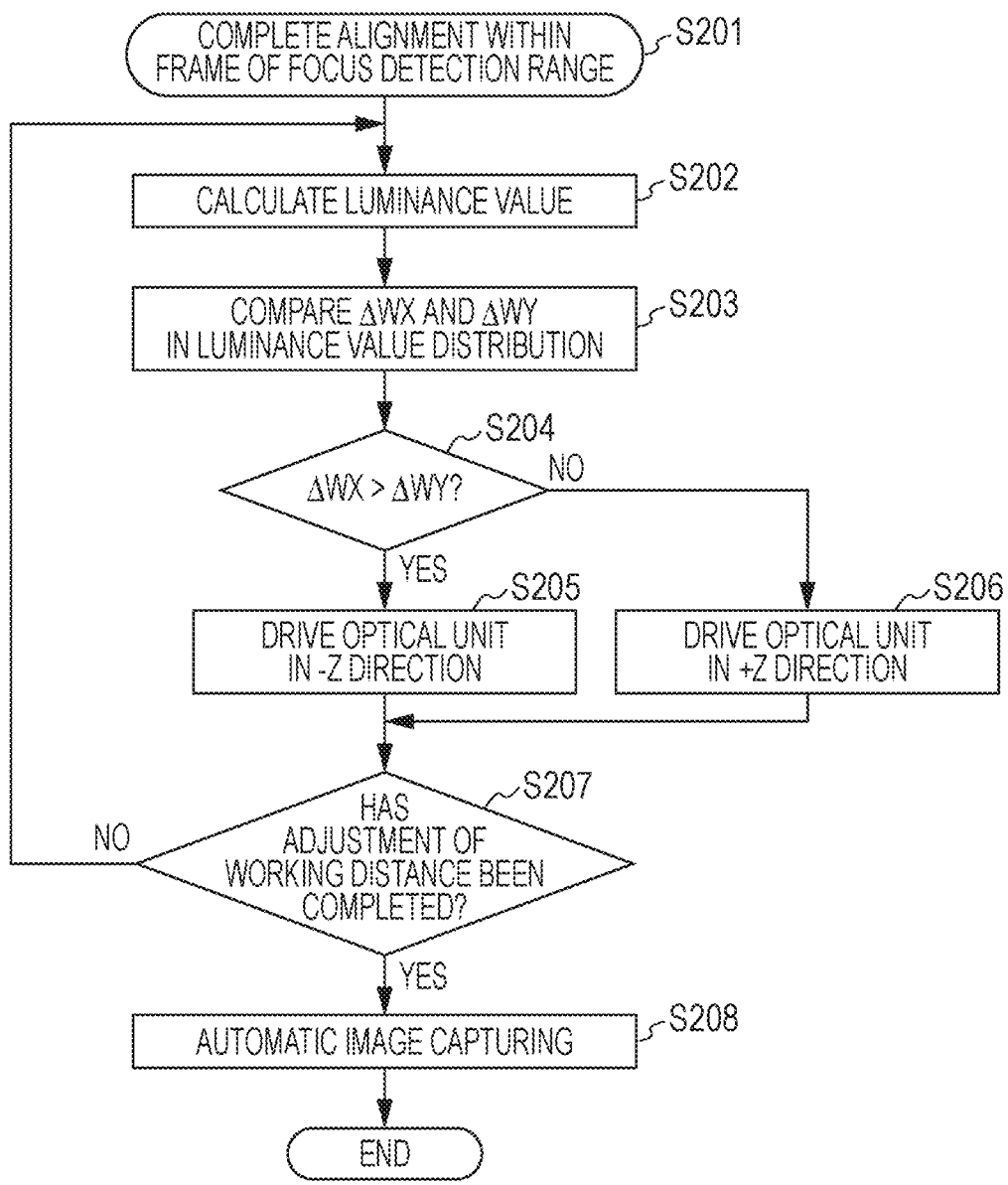

OPHTHALMOLOGIC APPARATUS, METHOD FOR CONTROLLING OPHTHALMOLOGIC APPARATUS, AND PROGRAM

BACKGROUND

1. Field

Aspects of the present invention generally relate to ophthalmologic apparatuses, methods for controlling ophthalmologic apparatuses, and programs.

2. Description of the Related Art

Among existing ophthalmologic apparatuses, in a fundus camera, for example, a working distance between an eye to be examined and the ophthalmologic apparatus in an optical axis direction is adjusted to an appropriate distance prior to capturing an image of a fundus of the eye to be examined. In one of the known methods for adjusting the working distance, a cornea reflection image of a target that has been projected on a cornea of an eye to be examined is observed on a monitor, and the target is manually brought into focus. In addition, known is a configuration in which an ophthalmologic apparatus automatically determines whether the working distance is appropriate based on information on a luminance value distribution of a cornea reflection image of a target that has been projected on a cornea of an eye to be examined and the ophthalmologic apparatus automatically captures an image upon determining that the working distance is appropriate.

Japanese Patent Laid-Open No. 06-046999 discloses a fundus camera in which two types of targets, namely a finite distance target of a finite distance and an infinite distance target, are projected on an eye to be examined and the working distance is calculated from the positional relationship between the finite distance target and the infinite distance target so as to determine whether the working distance is appropriate.

In addition, Japanese Patent Laid-Open No. 07-031590 discloses a fundus camera in which optical members are disposed such that a target is offset when the working distance is not appropriate and the target matches when the working distance becomes appropriate and whether the working distance is appropriate is determined by determining an offset of the target.

It is difficult, however, for an examiner to determine whether the working distance between the eye to be examined and the ophthalmologic apparatus is greater or less than an appropriate working distance at a point at which the examiner is trying to adjust the working distance while observing a reflection image of a target on a monitor. Thus, the examiner simply determines that the working distance is not appropriate in a state in which the target is out of focus while observing the reflection image of the target projected on the monitor and moves the apparatus body back and forth in the optical axis direction. Based on the result of such an operation, the examiner determines whether the working distance between the eye to be examined and the apparatus body is greater or less than the appropriate working distance and then moves the apparatus body so as to bring the working distance to an appropriate working distance. The examiner can thus finish adjusting the working distance by repeating such operations. Accordingly, it is difficult to promptly capture an image of the fundus of the eye to be examined.

SUMMARY

According to an aspect of the present invention, an ophthalmologic apparatus includes an optical unit configured to capture an image of an eye to be examined, a target projection unit configured to project a target, the target being used to adjust a working distance between the eye to be examined and the optical unit, and a determination unit configured to determine whether the working distance is appropriate based on a cornea reflection image from the eye to be examined captured by the optical unit. In the ophthalmologic apparatus, the determination unit determines a direction in which the working distance is to be adjusted so as to bring the target into focus based on an influence of astigmatism contained in the cornea reflection image captured by the optical unit.

Further features of the present disclosure will become apparent from the following description of exemplary embodiments with reference to the attached drawings.

BRIEF DESCRIPTION OF THE DRAWINGS

FIG. 13 is another flowchart for describing the exemplary embodiment.

DESCRIPTION OF THE EMBODIMENTS

Hereinafter, an ophthalmologic apparatus according to an exemplary embodiment will be described in detail with reference to FIGS. 1A to 13. A fundus camera is illustrated as the ophthalmologic apparatus according to the exemplary embodiment. The ophthalmologic apparatus according to the exemplary embodiment, however, is not limited to the fundus camera. The exemplary embodiment can be applied to various other ophthalmologic apparatuses such as various types of ophthalmologic photographing apparatuses and ocular refractivity measurement apparatuses.

Figure 1A:
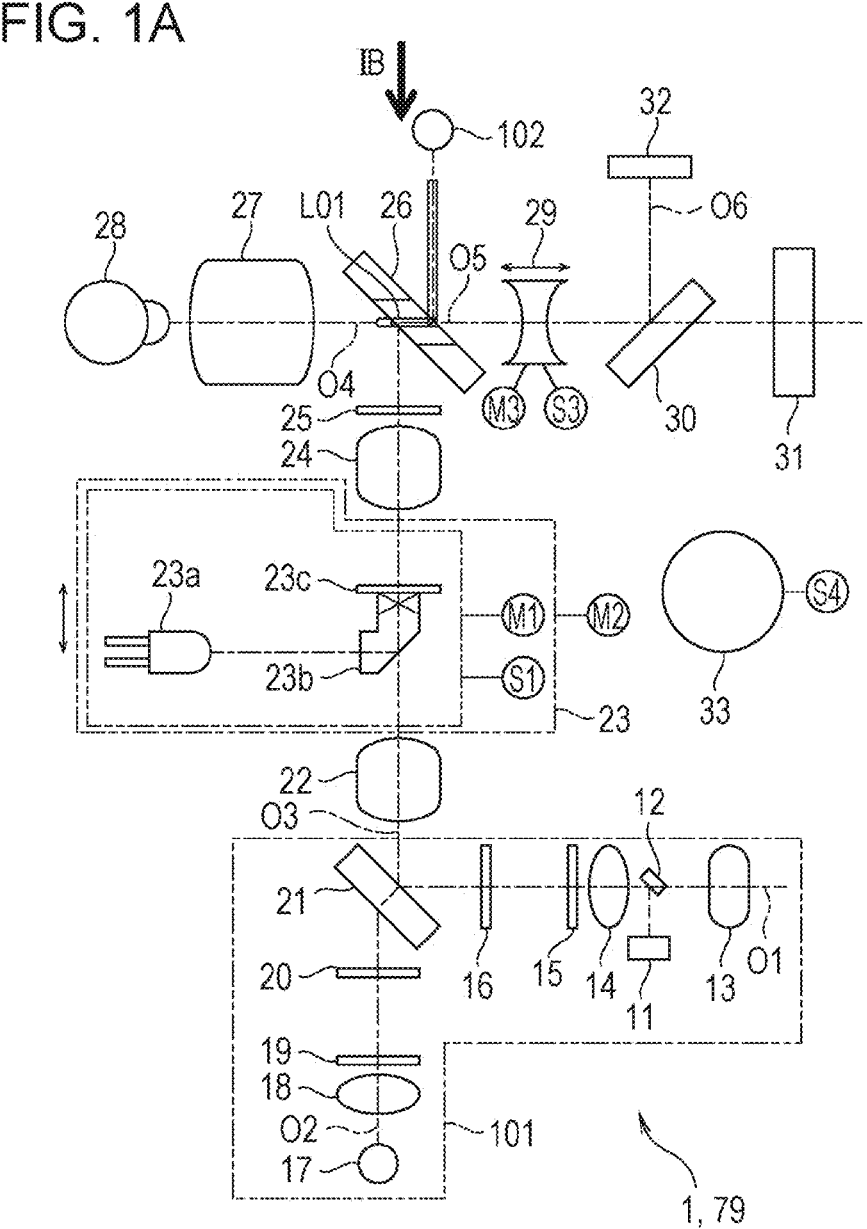
FIGS. 1A and 1B are schematic configuration diagrams for describing an exemplary embodiment.
Figure 1B:
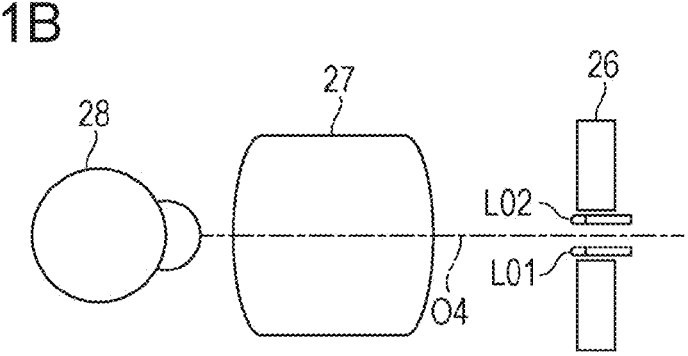

First, with reference to FIGS. 1A and 1B, a general configuration of a fundus camera 1, which serves as the ophthalmologic apparatus according to the exemplary embodiment, will be described. FIGS. 1A and 1B schematically illustrate the general configuration of the fundus camera 1.

The fundus camera 1 includes an imaging light source section O1, an observation light source section O2, an illumination optical system O3, an imaging/observation optical system O4, an imaging optical system O5, and an internal fixation lamp section O6. The imaging light source section O1 and the observation light source section O2 each emit a light beam. The emitted light beams travel through the illumination optical system O3 and the imaging/observation optical system O4 and illuminate a fundus portion of an eye 28 to be examined. A reflected beam (optical image) from the illuminated fundus portion of the eye 28 travels through the imaging/observation optical system O4 and the imaging optical system O5 and is imaged on an image sensor element 31.

The imaging light source section O1 generates white light ring illumination through the following configuration.

The imaging light source section O1 includes a light quantity detection unit 11. A known sensor such as an SPC and a PD which utilizes photoelectric conversion can be used as the light quantity detection unit 11. The imaging light source section O1 further includes a mirror 12. The mirror 12 is formed by a glass plate on which aluminum or silver is deposited, an aluminum plate, or the like. The imaging light source section O1 further includes an imaging light source 13. The imaging light source 13 includes a glass tube that is filled with Xe and emits light as a voltage is applied to the glass tube. Light emitted from the imaging light source 13 can provide white light that has an intensity sufficient for obtaining a fundus image at the time of imaging. The imaging light source section O1 further includes an imaging condenser lens 14. A typical spherical lens is used as the imaging condenser lens 14. The imaging light source section O1 further includes an imaging ring slit 15. The imaging ring slit 15 is a flat plate in which a ring-shaped aperture is formed. The imaging light source section O1 further includes an imaging crystalline lens baffle 16. The imaging crystalline lens baffle 16 is also a flat plate in which a ring-shaped aperture is formed.

The imaging condenser lens 14 condenses the light beam emitted from the imaging light source 13 so as to be focused at the fundus of the eye 28. The imaging ring slit 15 shapes the condensed light beam such that the light beam has a ring shaped section when passing through an anterior eye portion of the eye 28. The imaging crystalline lens baffle 16 limits the light beam to be projected onto a crystalline lens of the eye 28 so as to prevent an unwanted reflected beam from the crystalline lens of the eye 28 from appearing in a fundus image.

The observation light source section O2 generates infrared light ring illumination through the following configuration.

The observation light source section O2 includes an observation light source 17. The observation light source 17 is a light source such as a halogen lamp and an LED which is capable of continuous light emission and emits infrared light through the device characteristics or filtering. The observation light source unit O2 further includes an observation condenser lens 18. The observation condenser lens 18 is a typical spherical lens. The observation light source unit O2 further includes an observation ring slit 19. The observation ring slit 19 is a flat plate in which a ring-shaped aperture is formed. The observation light source unit O2 further includes an observation crystalline lens baffle 20. The observation crystalline lens baffle 20 is also a flat plate in which a ring-shaped aperture is formed. The observation light source section O2 differs from the imaging light source section O1 only in the type of the light source. In other words, the observation condenser lens 18 condenses the light beam, and the observation ring slit 19 shapes the light beam such that the light beam has a ring shaped section when passing through the anterior eye portion. In addition, the observation crystalline lens baffle 20 prevents an unwanted reflected beam from the crystalline lens from appearing in the fundus image.

The illumination optical system O3 relays the light beams formed through the imaging light source section O1 and the observation light source section O2 and also generates a target image to be used for bringing the fundus image into focus.

The illumination optical system O3 includes a dichroic mirror 21. The dichroic mirror 21 transmits infrared light and reflects visible light. The dichroic mirror 21 reflects the light beam of visible light generated through the imaging light source section O1 and transmits the light beam of infrared light generated through the observation light source section O2 to thus guide the light beams into the illumination optical system O3. The illumination optical system O3 further includes a first illumination relay lens 22 and a second illumination relay lens 24. The first illumination relay lens 22 and the second illumination relay lens 24 collectively cause the ring illumination to be imaged on the eye 28.

The illumination optical system O3 is provided with a split unit 23. The split unit 23 includes a focus target light source 23a for projecting a focus target, a prism 23b for splitting the light, and a focus target mask 23c that indicates an external shape of the focus target.

The split unit 23 further includes a moving mechanism that causes the focus target to be shifted in an optical axis direction, and an inserting/extracting mechanism that retracts the split unit 23 from the illumination optical system O3 at the time of imaging. At the time of observation, the inserting/extracting mechanism places the split unit 23 in the illumination optical system O3, and the moving mechanism moves the split unit 23 in directions indicated by a double-headed arrow in FIG. 1A. The moving mechanism includes a split shift driving motor M1 and a split position sensor S1. The split shift driving motor M1 shifts the split unit 23 to bring the focus target into focus. The split position sensor S1 detects a position at which the split unit 23 is stopped. The inserting/extracting mechanism includes a split insertion/extraction driving motor M2. The split insertion/extraction driving motor M2 inserts or extracts the split unit 23 into or from the illumination optical system O3. To be more specific, the split insertion/extraction driving motor M2 places the split unit 23 in the illumination optical system O3 when a fundus is to be observed, so that the focus target is projected in the fundus image. Meanwhile, the split insertion/extraction driving motor M2 retracts the split unit 23 from the illumination optical system O3 at the time of imaging, so that the focus target does not appear in the captured image. The illumination optical system O3 further includes a cornea baffle 25. The cornea baffle 25 prevents an unwanted reflected beam from the cornea of the eye 28 from appearing in the fundus image.

The imaging/observation optical system O4 projects the illumination light beam on the fundus of the eye 28 and also derives the fundus image of the eye 28.

The imaging/observation optical system O4 includes a perforated mirror 26. The perforated mirror 26 has an opening formed in a center portion thereof, and the outer peripheral portion serves as a mirror portion. The light beam guided from the illumination optical system O3 is reflected by the mirror portion of the perforated mirror 26, and the reflected beam illuminates the fundus of the eye 28 through an objective lens 27. A reflected beam (fundus image) from the illuminated eye 28 travels back through the objective lens 27 and is guided to the imaging optical system O5 through the opening formed in the center portion of the perforated mirror 26.

In addition, a light beam from a light source 102 is guided into the imaging/observation optical system O4 via target projection units L01 and L02, which serve as light guiding members, and is then projected on the cornea of the eye 28 through the objective lens 27. A reflected beam from the eye 28 travels back through the objective lens 27 and is guided to the imaging optical system O5 through the opening formed in the center portion of the perforated mirror 26. Here, each of the target projection units L01 and L02 is disposed at a location that is in the vicinity of the perforated mirror 26 and that is spaced apart from the imaging/observation optical system O4 by a predetermined distance.

The imaging optical system O5 adjusts the focus of the fundus image of the eye 28 and causes the fundus image to be imaged on the image sensor element 31. The imaging optical system O5 includes a focusing lens 29. The focusing lens 29 serves to adjust the focal point of the imaging light beam that has passed through the opening formed in the center portion of the perforated mirror 26 and adjusts the focal point by being moving in directions indicated by a double-headed arrow in FIG. 1A. The imaging optical system O5 further includes a focusing lens driving motor M3 and a focusing lens position sensor S3. The focusing lens driving motor M3 and the focusing lens position sensor S3 drive the focusing lens 29 to adjust the focal point of the focusing lens 29 and also detect the position at which the focusing lens 29 is stopped. The image sensor element 31 subjects the imaged fundus image (optical image) to photoelectric conversion. An electric signal (analog signal) obtained by the image sensor element 31 is subjected to A/D conversion (converted into a digital signal) by an A/D conversion element 73 (refer to FIG. 2, omitted in FIG. 1A). In addition, this electric signal is displayed on a monitor 77 (refer to FIG. 2, omitted in FIG. 1A) at the time of infrared light observation and is recorded in a memory 74 (refer to FIG. 2, omitted in FIG. 1A) after imaging. Furthermore, the image sensor element 31 images (carries out photoelectric conversion on) cornea reflection images L1 and L2 of the target projection units L01 and L02.

The internal fixation lamp section O6 is provided in an optical path that is split from the imaging optical system O5 by a half-silvered mirror 30. An internal fixation lamp unit 32 is provided in an optical path of the imaging optical system O5 so as to oppose the half-silvered mirror 30. The internal fixation lamp unit 32 includes a plurality of LEDs and lights an LED that is located at a position corresponding to a fixation portion selected by an examiner (user) through a fixation lamp position specification member 66 (refer to FIG. 2). As an eye of a subject is fixed on the lit LED, the examiner (user) can obtain a fundus image in which the eye is directed in a desired direction.

The components described above are held in a single housing to constitute a fundus camera optical unit 79. The fundus camera optical unit 79 is mounted on a sliding table (not illustrated) and can be positioned relative to the eye 28.

Figure 2:
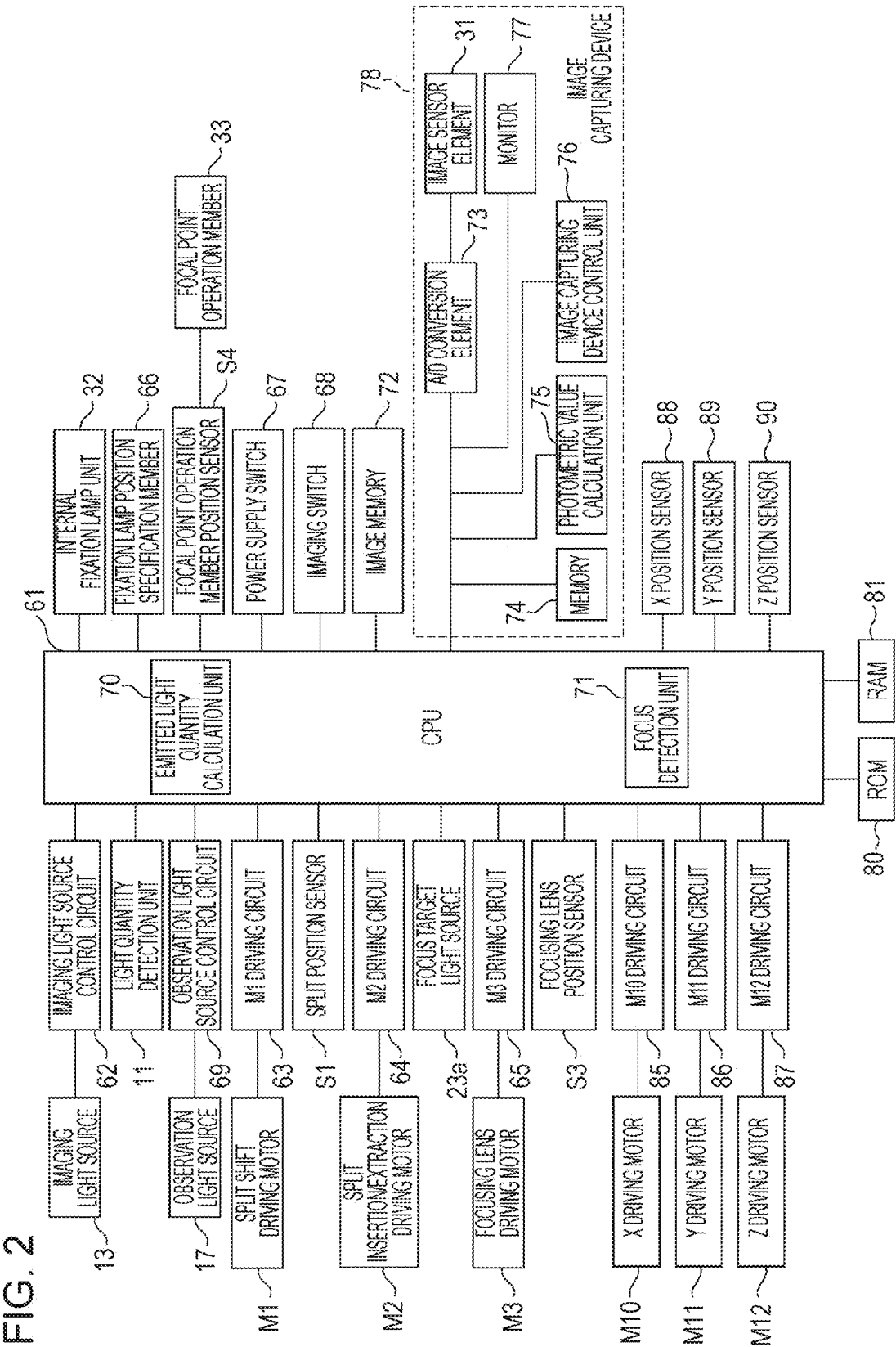
FIG. 2 is a functional block diagram for describing the exemplary embodiment.

With reference to FIG. 2, functional blocks of the fundus camera 1 will now be described. FIG. 2 illustrates functional blocks of the fundus camera 1 according to the exemplary embodiment.

The fundus camera 1 includes a CPU 61, a ROM 80, and a RAM 81. The ROM 80 stores a computer program for controlling the constituent elements of the fundus camera 1. The CPU 61 loads the computer program from the ROM 80, expands the computer program in the RAM 81, and executes the computer program. Through this, the constituent elements of the fundus camera 1 are controlled, and all of the operations described below are implemented. In addition, as the CPU 61 executes the computer program, the CPU 61 functions as an emitted light quantity calculation unit 70 and a focus detection unit 71.

An imaging light source control circuit 62, which is connected to the imaging light source 13, and an observation light source control circuit 69, which is connected to the observation light source 17, are connected to the CPU 61, which functions as the emitted light quantity calculation unit 70. The imaging light source control circuit 62 and the observation light source control circuit 69 control the imaging light source 13 and the observation light source 17, respectively, so as to adjust the quantity of light and to light up or light off the imaging light source 13 and the observation light source 17.

In addition, prior to imaging, the imaging light source control circuit 62 accumulates electric energy for causing the imaging light source 13 to emit light. At the time of imaging, the imaging light source control circuit 62 discharges the accumulated electric energy to cause the imaging light source 13 to emit light.

The light quantity detection unit 11 detects the quantity of light emitted from the imaging light source 13. The CPU 61, which functions as the emitted light quantity calculation unit 70, makes a calculation to determine whether the quantity of the emitted light detected by the light quantity detection unit 11 has reached a predetermined quantity. Upon the quantity of the emitted light reaching the predetermined quantity, the CPU 61 instructs the imaging light source 13 to stop emitting light through the imaging light source control circuit 62. Through this, the imaging light source 13 stops emitting light.

An M2 driving circuit 64 drives the split insertion/extraction driving motor M2 to insert and extract the split unit 23 into and from the illumination optical system O3 prior to and following imaging.

A power supply switch 67 is a switch (operation member) that allows the examiner (user) to select a power supply state of the fundus camera 1. An imaging switch 68 is a switch (operation member) that allows the examiner (user) to instruct the fundus camera 1 to carry out imaging.

A focal point operation member 33 is an operation member that is operated by the examiner (user) to adjust the focal point. Upon the examiner operating the focal point operation member 33, a focal point operation member position sensor S4 detects the position at which the focal point operation member 33 is stopped and outputs the result.

The fixation lamp position specification member 66 is an operation member that allows the examiner to specify which one of the plurality of LEDs included in the internal fixation lamp unit 32 is to be lit. Upon the examiner operating the fixation lamp position specification member 66, the CPU 61 lights an LED located at a position specified through the operation.

An M1 driving circuit 63 drives the split shift driving motor M1 such that the split unit 23 moves to a location corresponding to an output from the focal point operation member position sensor S4. An M3 driving circuit 65 drives the focusing lens driving motor M3 such that the focusing lens 29 moves to a location corresponding to an output from the focal point operation member position sensor S4, as in the M1 driving circuit 63.

Note that the fundus camera 1 in the exemplary embodiment can adjust the focus through a manual focusing mode in which the examiner manually adjusts the focus or through an automatic focusing mode in which the focus is adjusted automatically.

While the fundus camera 1 is in the manual focusing mode, the M1 driving circuit 63 and the M3 driving circuit 65 control the split shift driving motor M1 and the focusing lens driving motor M3, respectively, in accordance with the outputs from the focal point operation member position sensor S4.

Meanwhile, when the fundus camera 1 is in the automatic focusing mode, the CPU 61 controls the focusing lens driving motor M3 through the M3 driving circuit 65 based on the result of detection of the focus detection unit 71 in the CPU 61.

In addition, the fundus camera 1 includes an automatic imaging mode. While the fundus camera 1 operates in the automatic imaging mode, the CPU 61 determines the focusing states of the cornea reflection images L1 and L2 of the target projection units L01 and L02 from the eye 28 based on the result of detection of the focus detection unit (CPU 61) and causes the imaging light source 13 to emit light through the imaging light source control circuit 62.

An image capturing device 78 includes the image sensor element 31, the A/D conversion element 73, the memory 74, a photometric value calculation unit 75, the monitor 77, and an image capturing device control unit 76. Each of the constituent elements of the image capturing device 78 is connected to the CPU 61.

The image capturing device control unit 76 controls each of the constituent elements of the image capturing device 78.

The A/D conversion element 73 converts an output of the image sensor element 31 to a digital signal. The output, which has been converted to a digital signal, is stored in the memory 74 and is also outputted to the photometric value calculation unit 75. The monitor 77 can display an infrared light observation image or a visible light image captured by the image sensor element 31.

The image capturing device 78 is detachably mounted to the housing of the fundus camera optical unit 79 through a mount portion (not illustrated).

An image memory 72 is connected to the CPU 61, and a still image captured by the image sensor element 31 is stored in the image memory 72 in the form of a digital image.

Additionally, the fundus camera 1 includes an operation input unit (not illustrated) that is to be operated by the examiner (user). Upon detecting the operation input unit being operated by the examiner, the CPU 61 carries out processing or an operation associated with the operation inputted through the operation input unit. The examiner can operate the fundus camera 1 or input various settings by operating the operation input unit.

Figure 3A:
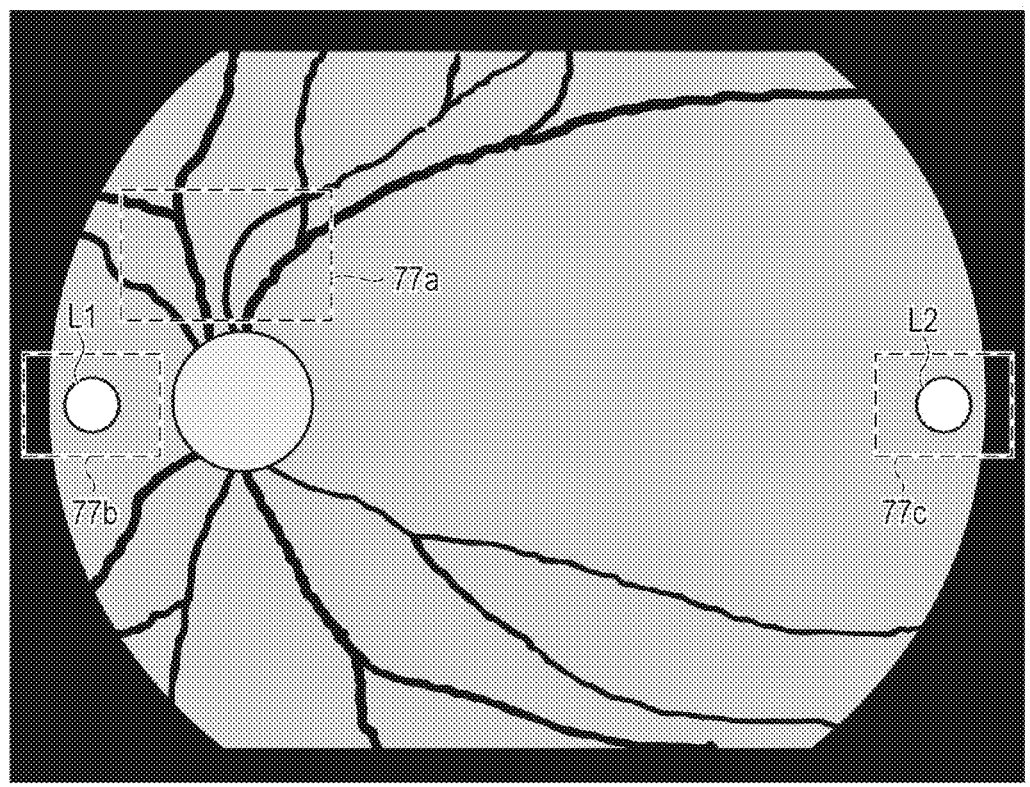
FIGS. 3A and 3B are illustrations of a fundus image and a cornea reflection image, respectively, of an eye to be examined which are projected on a monitor for describing the exemplary embodiment.
Figure 3B:
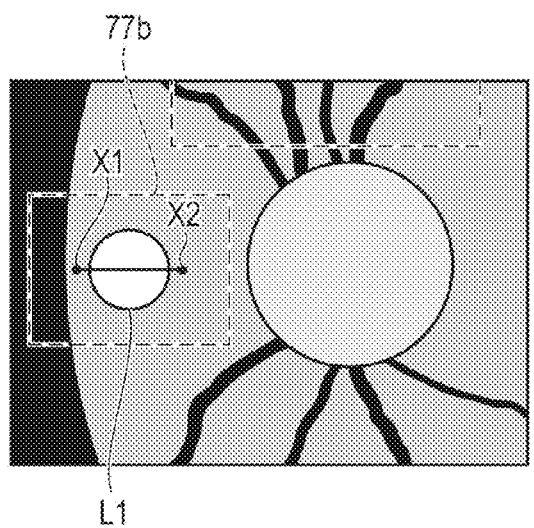

With reference to FIGS. 3A and 3B, a fundus image and a cornea reflection image of the eye 28 displayed on the monitor 77 will now be described. FIG. 3A illustrates an example of a display area of the monitor 77. As illustrated in FIG. 3A, the fundus image of the eye 28, focus detection ranges 77a, 77b, and 77c, and the cornea reflection images L1 and L2 of the eye 28 are displayed on the monitor 77. FIG. 3B is an enlarged view of the cornea reflection image L1 and the vicinity thereof. Here, the cornea reflection images L1 and L2 correspond to reflection images formed as the targets projected on the eye 28 by the target projection units L01 and L02 are reflected by the cornea.

When the fundus is to be observed, the CPU 61 displays, on the monitor 77, the fundus image obtained by the image capturing device 78 and also displays a frame portion of the focus detection range 77a so as to be superimposed on the fundus image. Through this, the focus detection range 77a is indicated to the examiner. In this manner, the focus detection range 77a can be indicated visually to the examiner, and thus operability of automatic focusing can be improved. Note that the focus detection range 77a can be modified through an operation by the examiner, and the examiner can set the focus detection range 77a to a specific site of the fundus of the eye 28 or to the entire fundus of the eye 28. Here, in a case in which the focus detection range 77a is set to the entire fundus, the CPU 61 automatically determines the focus detection range 77a.

Furthermore, when the fundus is to be observed, the CPU 61 displays, on the monitor 77, the fundus image obtained by the image capturing device 78 and also displays frame portions of the focus detection ranges 77b and 77c so as to be superimposed on the fundus image. Through this, the focus detection ranges 77b and 77c are indicated to the examiner. In this manner, focusing detection positions for the cornea reflection images L1 and L2 of the target projection units L01 and L02 from the eye 28 can be indicated visually to the examiner. Thus, operability in alignment, aside from the adjustment of the working distance between the eye 28 and the fundus camera optical unit 79, can be improved.

The focus detection unit 71 determines whether the working distance between the eye 28 and the fundus camera optical unit 79 is appropriate by determining whether the cornea reflection images L1 and L2 are in focus within the frames of the focus detection ranges 77b and 77c.

Figure 4:
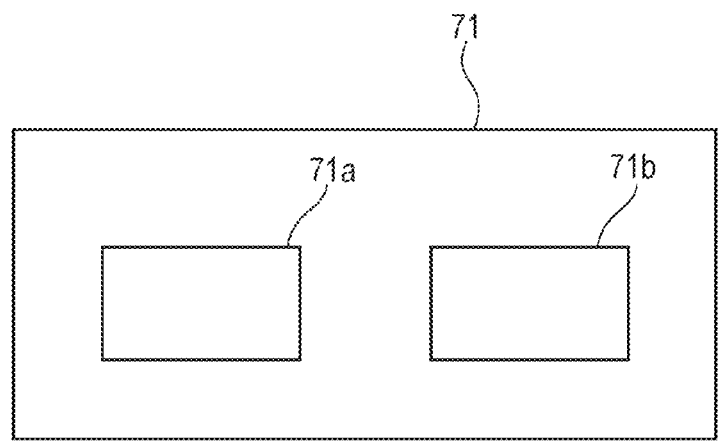
FIG. 4 is a schematic configuration diagram of a focus detection unit for describing the exemplary embodiment.
Figure 5:
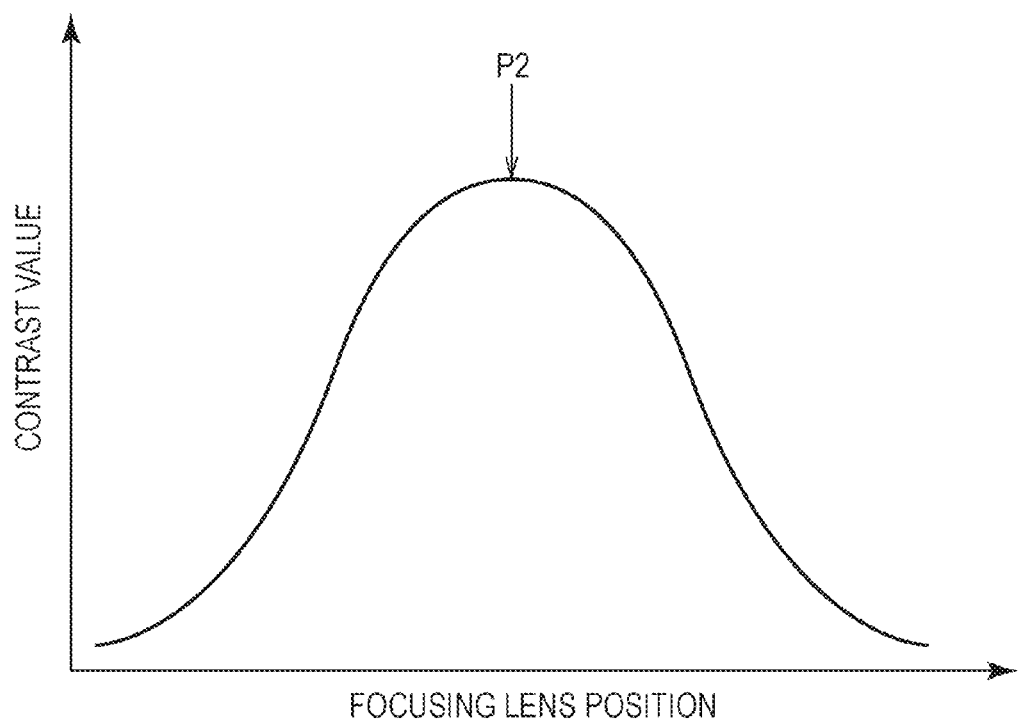
FIG. 5 is a diagram illustrating a principle of contrast detection for describing the exemplary embodiment.
Figure 6:
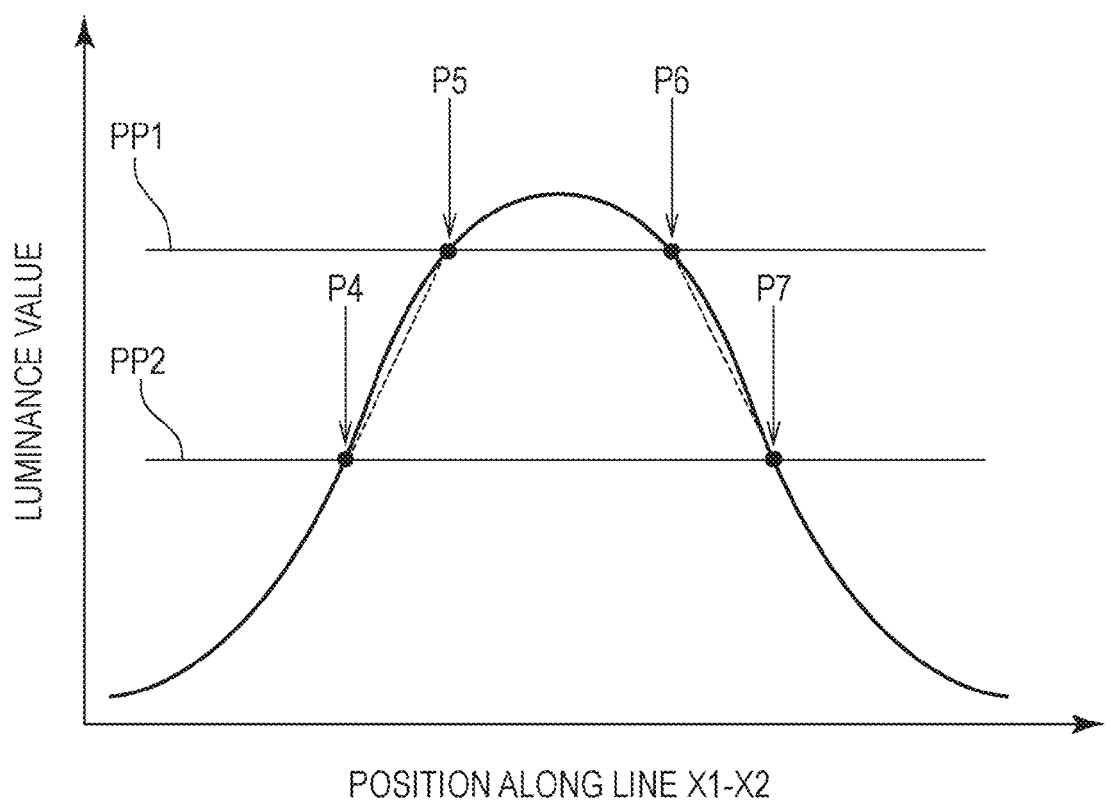
FIG. 6 is a diagram illustrating a principle of luminance value detection for describing the exemplary embodiment.

With reference to FIGS. 4 to 6, a general configuration of the focus detection unit 71, a principle of contrast detection, and a principle of luminance value detection will now be described. FIG. 4 is a schematic configuration diagram of the focus detection unit 71, for describing the exemplary embodiment. FIG. 5 is a diagram illustrating the principle of contrast detection, for describing the exemplary embodiment. FIG. 6 is a diagram illustrating the principle of luminance value detection, for describing the exemplary embodiment.

As illustrated in FIG. 4, the focus detection unit 71 is provided with a focus detection range determination unit 71a and a focus evaluation value storage unit 71b. The focus detection range determination unit 71a sets a specific position on the fundus of the eye 28 as a focus detection target. The examiner can set the focus detection range by operating the operation input unit (not illustrated) of the fundus camera 1. The focus evaluation value storage unit 71b stores a contrast value of the fundus image and the position of the focusing lens 29.

In the exemplary embodiment, the focus detection unit 71 detects the focus by detecting a contrast value of the fundus image obtained by imaging the imaging light beam.

In addition, the focus detection range determination unit 71a specifies the cornea reflection images L1 and L2 of the target projection units L01 and L02 from the eye 28 as focus detection position targets. The focus evaluation value storage unit 71b calculates focusing states from the luminance values of the cornea reflection images L1 and L2 from the eye 28 and evaluates the result. For example, the focus evaluation value storage unit 71b calculates a luminance value distribution along a scanning line X1-X2 indicated in FIG. 3B, evaluates the distribution, and stores the result of the evaluation. In the exemplary embodiment, the focus detection unit 71 detects the focuses in the cornea reflection images L1 and L2 by detecting the luminance values of the cornea reflection images L1 and L2.

FIG. 5 illustrates a graph for describing the principle of contrast detection and schematically illustrates a change of the contrast values with respect to the position of the focusing lens 29. The focusing lens 29 is moved by the focusing lens driving motor M3. As illustrated in FIG. 5, the contrast value reaches the maximum at a focus position P2. The contrast value is small at a position that is largely offset from the focus of the focusing lens 29. In the exemplary embodiment, by utilizing this principle of contrast detection, the focus can be detected without being affected by an aberration of the eye 28. In other words, the focus position P2 is a position in the fundus image projected on the monitor 77 which can be observed most sharply and coincides with a position in the fundus image projected on the monitor 77 which can be displayed most sharply after imaging.

Subsequently, detection of the luminance values of the cornea reflection images L1 and L2 of the target projection units L01 and L02 from the eye 28 will be described. FIG. 6 illustrates a luminance value distribution curve along the scanning line X1-X2 indicated in FIG. 3B. Here, for example, a value that is 80% of the calculated maximum luminance value is defined as PP1, and a value that is 50% of the calculated maximum luminance value is defined as PP2. In addition, points at which the luminance value distribution curve intersects with PP1 are defined as P5 and P6, and points at which the luminance value distribution curve intersects with PP2 are defined as P4 and P7. Whether the cornea reflection images L1 and L2 from the eye 28 are in focus can be determined by determining whether the absolute values of slopes of a line passing through P4 and P5 and a line passing through P6 and P7 (indicated by broken lines in FIG. 6) are equal to or greater than a predetermined value. If the absolute values of the slopes of these lines are equal to or greater than the predetermined value, the focus detection unit 71 determines that the cornea reflection images L1 and L2 are in focus at a predetermined level or higher. In such a case, the focus detection unit 71 determines that the working distance between the eye 28 and the fundus camera optical unit 79 is appropriate (within an appropriate range). In other words, the working distance falls within a predetermined range in which a flare does not appear in the fundus image projected on the monitor 77 after imaging.

Note that the specific values of PP1 and PP2 are not particularly limited. Furthermore, the predetermined value that serves as a reference for determining whether the images are in focus is not particularly limited, either.

Figure 7:
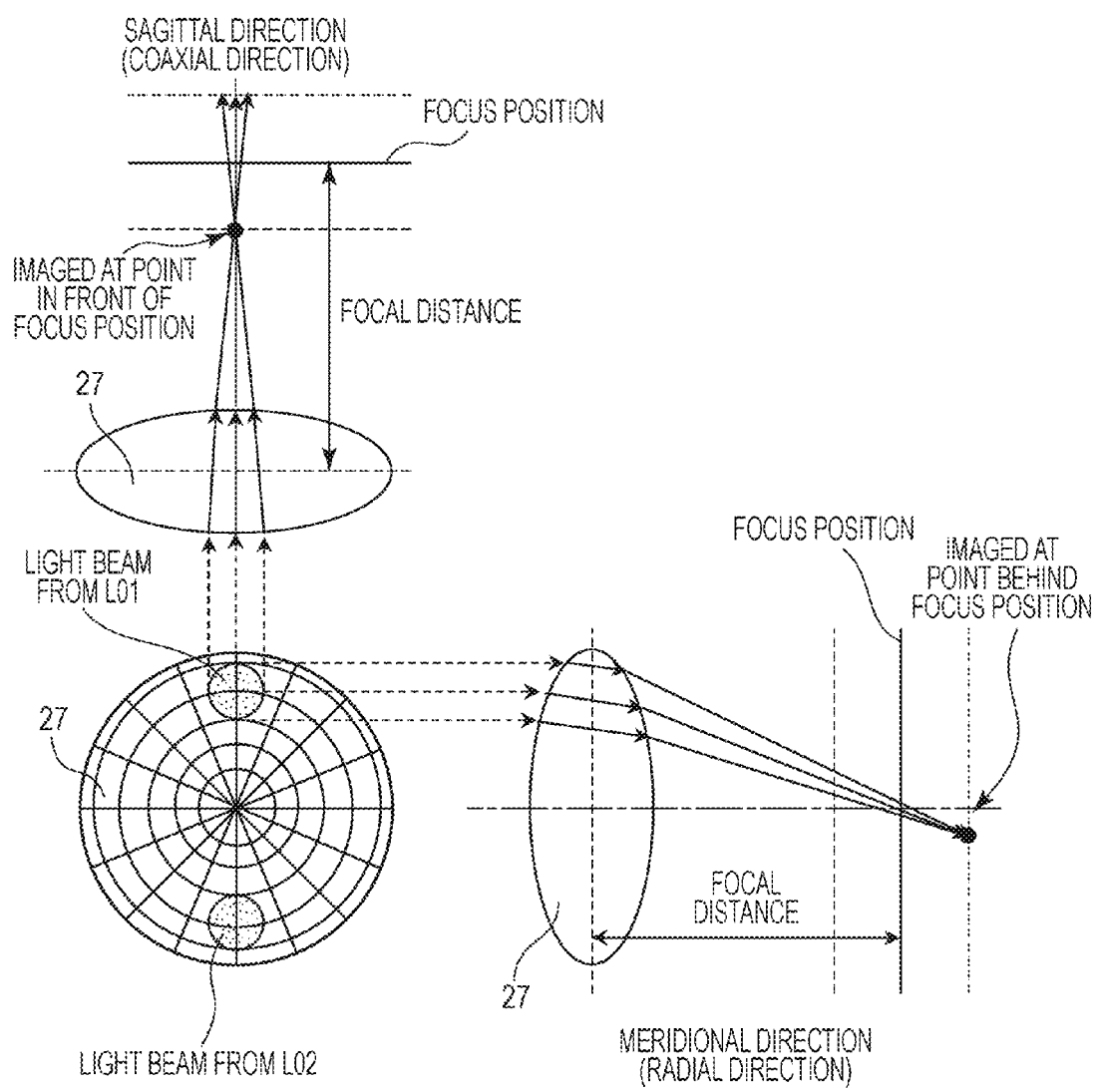
FIG. 7 is a conceptual diagram illustrating a difference in imaging position of a cornea reflection image L1 or L2 affected by astigmatism for describing the exemplary embodiment.
Figure 8A:
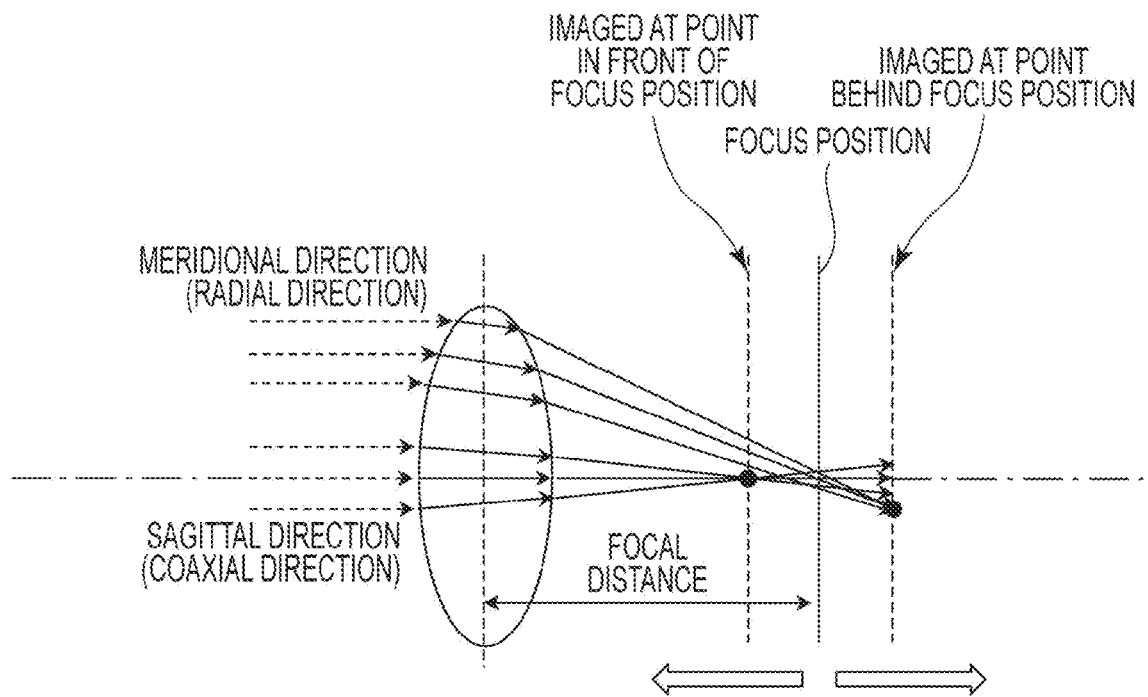
FIGS. 8A to 8C are conceptual diagrams illustrating a difference in blurring state of the cornea reflection image L1 or L2 affected by astigmatism for describing the exemplary embodiment.
Figure 8B:
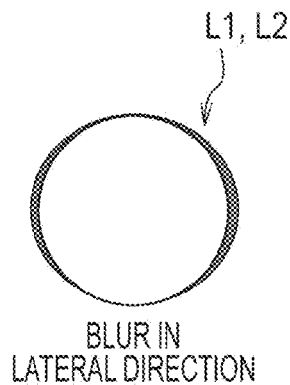
Figure 8C:
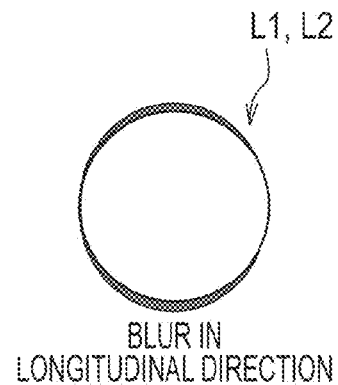

With reference to FIGS. 7 to 8C, influence of astigmatism on the cornea reflection images L1 and L2 in the adjustment of the working distance between the eye 28 and the fundus camera optical unit 79 will now be described. FIG. 7 is a conceptual diagram illustrating a difference in imaging position of the cornea reflection image L1 or L2 affected by astigmatism, for describing the exemplary embodiment. FIGS. 8A to 8C are conceptual diagrams illustrating a difference in blurring state of the cornea reflection image L1 or L2 affected by astigmatism, for describing the exemplary embodiment.

In the exemplary embodiment, each of the target projection units L01 and L02 is disposed at a location that is in the vicinity of the perforated mirror 26 and that is spaced apart from the imaging/observation optical system O4 by a predetermined distance. Thus, as illustrated in FIGS. 1A, 1B, and 7, each of the light beams guided via the target projection units L01 and L02 passes through a peripheral portion of the objective lens 27. The light beam that passes through the peripheral portion of the objective lens 27 is affected by the characteristics of astigmatism of the objective lens 27, or in other words, by astigmatism generated by a difference in curvature depending on the directions within the same lens. Thus, the imaging position of the light beam guided via the target projection unit L01 or L02 varies depending on the direction within the objective lens 27. This influence will be described using an example illustrated in FIG. 7. The light beam from the target projection unit L01 which passes through the peripheral portion of the objective lens 27 is imaged, in a meridional direction (radial direction) of the objective lens 27, at a point that is behind the focus position of the objective lens 27 and is imaged, in a sagittal direction (coaxial direction) of the objective lens 27, at a point that is in front of the focus position of the objective lens 27. As a result, as illustrated in FIGS. 8A and 8C, the cornea reflection image L1 or L2 of the target is imaged, in a lateral direction, at a point that is behind the focus position of the objective lens 27 and is thus blurred in a longitudinal direction. In other words, portions that are out of focus are generated at upper and lower portions of the cornea reflection image L1 or L2 of the target. As illustrated in FIGS. 8A and 8B, the cornea reflection image L1 or L2 of the target is imaged, in the longitudinal direction, at a point that is in front of the focus position of the objective lens 27 and is thus blurred in the lateral direction. In other words, portions that are out of focus are generated at right and left portions of the cornea reflection image L1 or L2 of the target.

Thus far, the influence of astigmatism on the cornea reflection image L1 or L2 in the adjustment of the working distance between the eye 28 and the fundus camera optical unit 79 has been described with reference to FIGS. 7 to 8C.

Figure 9A:
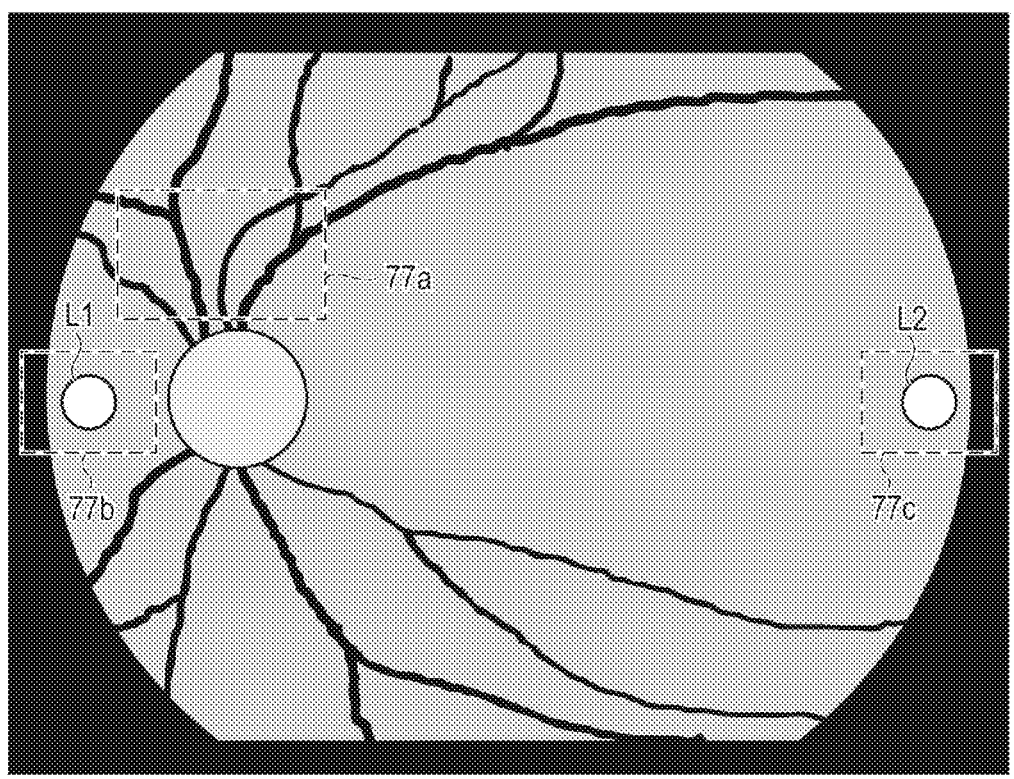
FIGS. 9A and 9B are illustrations of a fundus image and a cornea reflection image of an eye to be examined which are projected on a monitor for describing the exemplary embodiment.
Figure 9B:
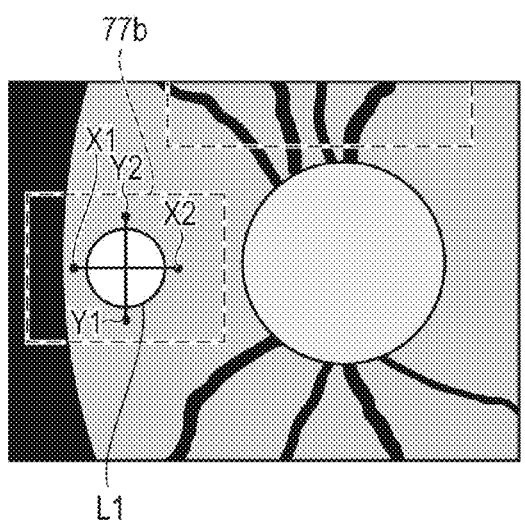
Figure 10A:
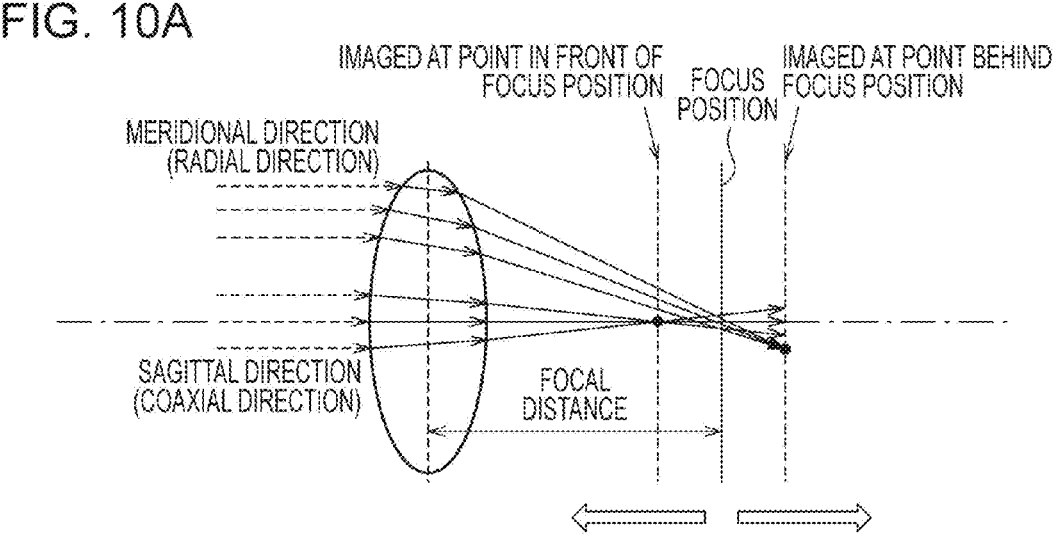
FIGS. 10A to 10C illustrate scanning lines for calculating a blurring state and a luminance value of a cornea reflection image projected on a monitor for describing the exemplary embodiment.
Figure 10B:
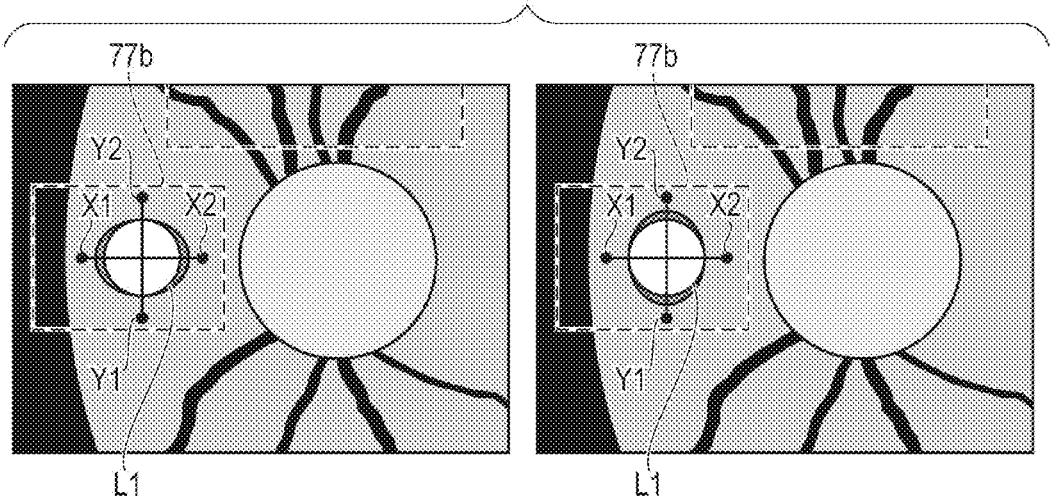
Figure 10C:
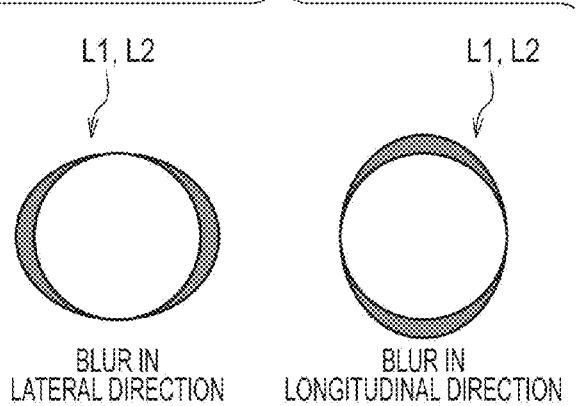
Figure 11A:
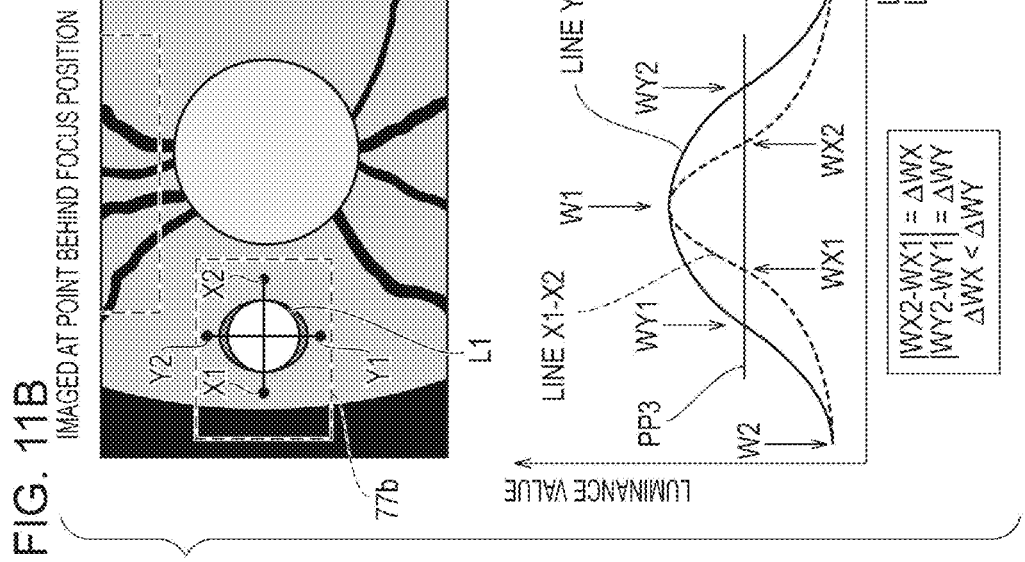
FIGS. 11A and 11B each illustrate a luminance value distribution that is based on the illustrations in FIGS. 10A to 10C for describing the exemplary embodiment.
Figure 11B:
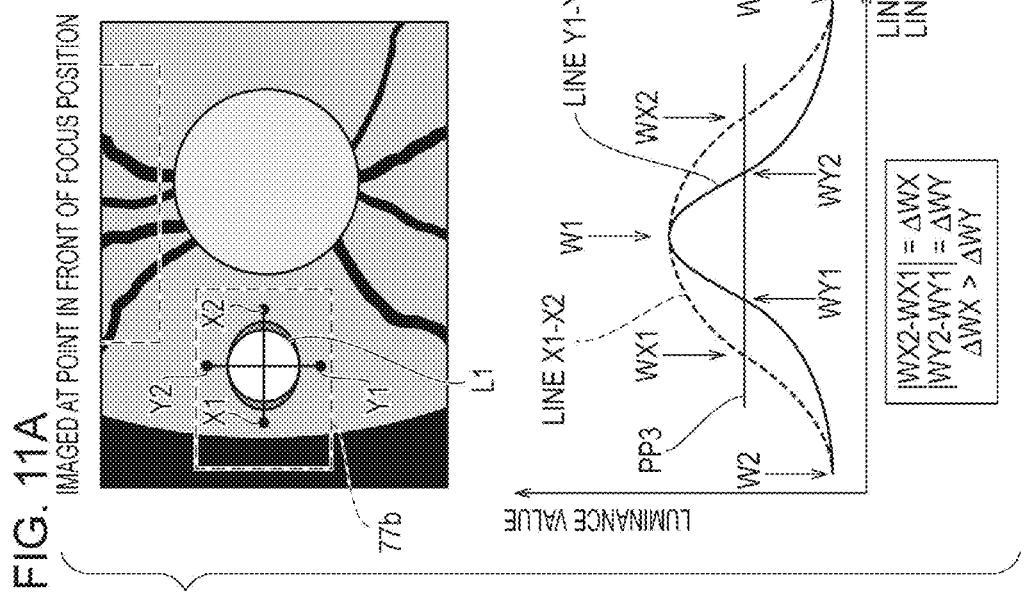

With reference to FIGS. 9A to 11B, the adjustment of the working distance between the eye 28 and the fundus camera optical unit 79 will now be described. FIGS. 9A and 9B illustrate an example of the fundus image of the eye 28 and examples of the cornea reflection images L1 and L2 projected on the monitor 77. FIGS. 10A to 10C illustrate scanning lines for calculating the blurring state and the luminance value of the cornea reflection images L1 and L2l projected on the monitor 77. FIGS. 11A and 11B illustrate examples of luminance value distributions based on FIGS. 10A to 10C.

In the exemplary embodiment, as illustrated in FIG. 9A, when the fundus is to be observed, the frame portions of the focus detection ranges 77b and 77c are displayed on the monitor 77 so as to be superimposed on the fundus image obtained by the image capturing device 78. Through this, the focus detection ranges 77b and 77c are indicated to the examiner. In addition, as illustrated in FIG. 9B, for example, while using the cornea reflection image L1 of the eye 28 as an example, a scanning line extending in the lateral direction for calculating the luminance value of the cornea reflection image L1 is defined as a scanning line X1-X2, and a scanning line extending in the longitudinal direction is defined as a scanning line Y1-Y2. In FIGS. 9A and 9B, the cornea reflection image L1 of the eye 28 is substantially in focus, and there is no significant difference between the blurring state in the lateral direction and the blurring state in the longitudinal direction.

As described with reference to FIGS. 8A to 8C, in FIGS. 10A to 10C, the blurring state of the cornea reflection image L1 of the eye 28 imaged at a point that is in a front of the focus position of the objective lens 27 differs from the blurring state of the cornea reflection image L1 image at a point that is behind the focus position of the objective lens 27. Here, as described with reference to FIG. 9B, X1-X2 represents the scanning line in the lateral direction for calculating the luminance value of the cornea reflection image L1 of the eye 28, and Y1-Y2 represents the scanning line in the longitudinal direction.

As illustrated in FIGS. 11A and 11B, the luminance value distributions along the scanning line X1-X2 in the lateral direction and the scanning line Y1-Y2 in the longitudinal direction differ in tendency between at a point that is in front of the focus position of the objective lens 27 and at a point that is behind the focus position.

First, a case in which the cornea reflection image L1 is imaged at a point that is in front of the focus position of the objective lens 27 will be described. This is a case in which the working distance between the eye 28 and the fundus camera optical unit 79 is smaller than an appropriate distance. In such a case, as illustrated in FIG. 11A, the cornea reflection image L1 from the eye 28 is blurred in the lateral direction (i.e., portions that are out of focus are generated at sides). Thus, the luminance value distribution shows a gentle curve along the scanning line X1-X2 in the lateral direction and a sharp curve along the scanning line Y1-Y2 in the longitudinal direction. Here, for example, a value that is 50% of the calculated maximum luminance value is defined as PP3, and points at which the scanning line X1-X2 and the scanning line Y1-Y2 intersect with PP3 are defined as WX1, WX2, WY1, and WY2. An absolute value of the distance between WX1 and WX2 is defined as |WX2−WX1|=ΔWX, and an absolute value of the distance between WY1 and WY2 is defined as |WY2−WY1|=ΔWY. In this case, as illustrated in FIG. 11A, ΔWX is greater than ΔWY. In other words, in a case in which the working distance between the eye 28 and the fundus camera optical unit 79 is smaller than an appropriate distance, ΔWX becomes greater than ΔWY.

The focus evaluation value storage unit 71b calculates the luminance value distribution along the scanning line X1-X2 in the lateral direction and the luminance value distribution along the scanning line Y1-Y2 in the longitudinal direction. The focus evaluation value storage unit 71b then compares ΔWX and ΔWY, as described above. If the evaluation yields that ΔWX is greater than ΔWY, the CPU 61 displays, on the monitor 77, an indication that the working distance between the eye 28 and the fundus camera optical unit 79 is smaller than the appropriate distance. Thus, the examiner is prompted to move the fundus camera optical unit 79 away from the eye 28 in the optical axis direction in order to bring the working distance to the appropriate distance. The direction in which the fundus camera optical unit 79 is moved away from the eye 28 is defined as a −Z direction.

Subsequently, a case in which the cornea reflection image L1 is imaged at a point that is behind the focus position of the objective lens 27 will be described. This is a case in which the working distance between the eye 28 and the fundus camera optical unit 79 is greater than the appropriate distance. As illustrated in FIG. 11B, in a case in which the working distance between the eye 28 and the fundus camera optical unit 79 is greater than the appropriate distance, ΔWX is smaller than ΔWY. In such a case, as illustrated in FIG. 11B, the cornea reflection image L1 from the eye 28 is blurred in the longitudinal direction (i.e., portions that are out of focus are generated at upper and lower portions). When the evaluation by the focus evaluation value storage unit 71b yields that ΔWX is smaller than ΔWY, the CPU 61 displays, on the monitor 77, an indication that the working distance between the eye 28 and the fundus camera optical unit 79 is greater than the appropriate distance. Thus, the examiner is prompted to move the fundus camera optical unit 79 to approach the eye 28 in the optical axis direction in order to bring the working distance to the appropriate distance. The direction in which the fundus camera optical unit 79 is moved to approach the eye 28 is defined as a +Z direction.

In this manner, the determination is made as to which direction the fundus camera optical unit 79 is to be moved (moving direction) in order to bring the working distance to the appropriate distance based on the positions of the portions that are out of focus. The examiner is then notified of the result of the determination through the monitor 77, helping the examiner to adjust the working distance promptly.

Although the exemplary embodiment has been described using two cornea reflection images L1 and L2 from the eye 28, there may be a single cornea reflection image from the eye 28.

In addition, although a configuration in which the examiner manually adjusts the working distance of the fundus camera optical unit 79 has been illustrated in the preceding description, a configuration in which the working distance is adjusted automatically may instead be employed. Here, a configuration that allows the fundus camera optical unit 79 to operate automatically will be described.

As illustrated in FIG. 2, the fundus camera 1 includes an X driving motor M10 that drives the fundus camera optical unit 79 in the horizontal direction, a Y driving motor M11 that drives the fundus camera optical unit 79 in the vertical direction, and a Z driving motor M12 that drives the fundus camera optical unit 79 in the optical axis direction. The X driving motor M10 is connected to the CPU 61 through an M10 driving circuit 85. The Y driving motor M11 is connected to the CPU 61 through an M11 driving circuit 86. The Z driving motor M12 is connected to the CPU 61 through an M12 driving circuit 87.

The fundus camera 1 further includes an X position sensor 88 that detects the position of the fundus camera optical unit 79 in the horizontal direction, a Y position sensor 89 that detects the position of the fundus camera optical unit 79 in the vertical direction, and a Z position sensor 90 that detects the position of the fundus camera optical unit 79 in the optical axis direction. These position sensors 88, 89, and 90 are each connected to the CPU 61 and can each notify the CPU 61 of the result of the detection.

First, the CPU 61 causes the cornea reflection images L1 and L2 from the eye 28 to fit within the frames of the focus detection ranges 77b and 77c, respectively, which have been determined by the focus detection range determination unit 71a. To be more specific, the CPU 61 instructs the M10 driving circuit 85 and the M11 driving circuit 86 to drive the X driving motor M10 and Y driving motor M11, respectively, by using the results of the detection by the X position sensor 88 and the Y position sensor 89. The M10 driving circuit 85 and the M11 driving circuit 86 drive the X driving motor M10 and the Y driving motor M11, respectively. Through this, the cornea reflection images L1 and L2 from the eye 28 can be made to fit within the frames of the focus detection ranges 77b and 77c, respectively.

Subsequently, the focus evaluation value storage unit 71b calculates the values of ΔWX and ΔWY and compares the values. If ΔWX is greater than ΔWY, the CPU 61 instructs the M12 driving circuit 87 to move the fundus camera optical unit 79 in a direction away from the eye 28. The M12 driving circuit 87 moves the Z driving motor M12 in the stated direction in accordance with the instruction from the CPU 61. Meanwhile, if ΔWX is smaller than ΔWY, the CPU 61 instructs the M12 driving circuit 87 to move the fundus camera optical unit 79 in a direction approaching the eye 28. The M12 driving circuit 87 moves the Z driving motor M12 in the stated direction in accordance with the instruction from the CPU 61.

With such a configuration, unnecessary operations can be eliminated in the alignment for adjusting the working distance between the eye 28 and the fundus camera optical unit 79. Accordingly, the alignment can be completed promptly.

Although the determination as to whether the imaging position is located in front of or behind the focus position is made based on the values of ΔWX and ΔWY in the exemplary embodiment, an exemplary embodiment is not limited to this method. For example, the magnitude of the slope at a rise or a fall of the luminance value distribution may be employed as an evaluation value for the comparison. Alternatively, the magnitude of the integrated value (area) of the luminance value distribution may be employed as an evaluation value for the comparison.

Thus far, the adjustment of the working distance between the eye 28 and the fundus camera optical unit 79 has been described with reference to FIGS. 9A to 11B.

Figure 12:
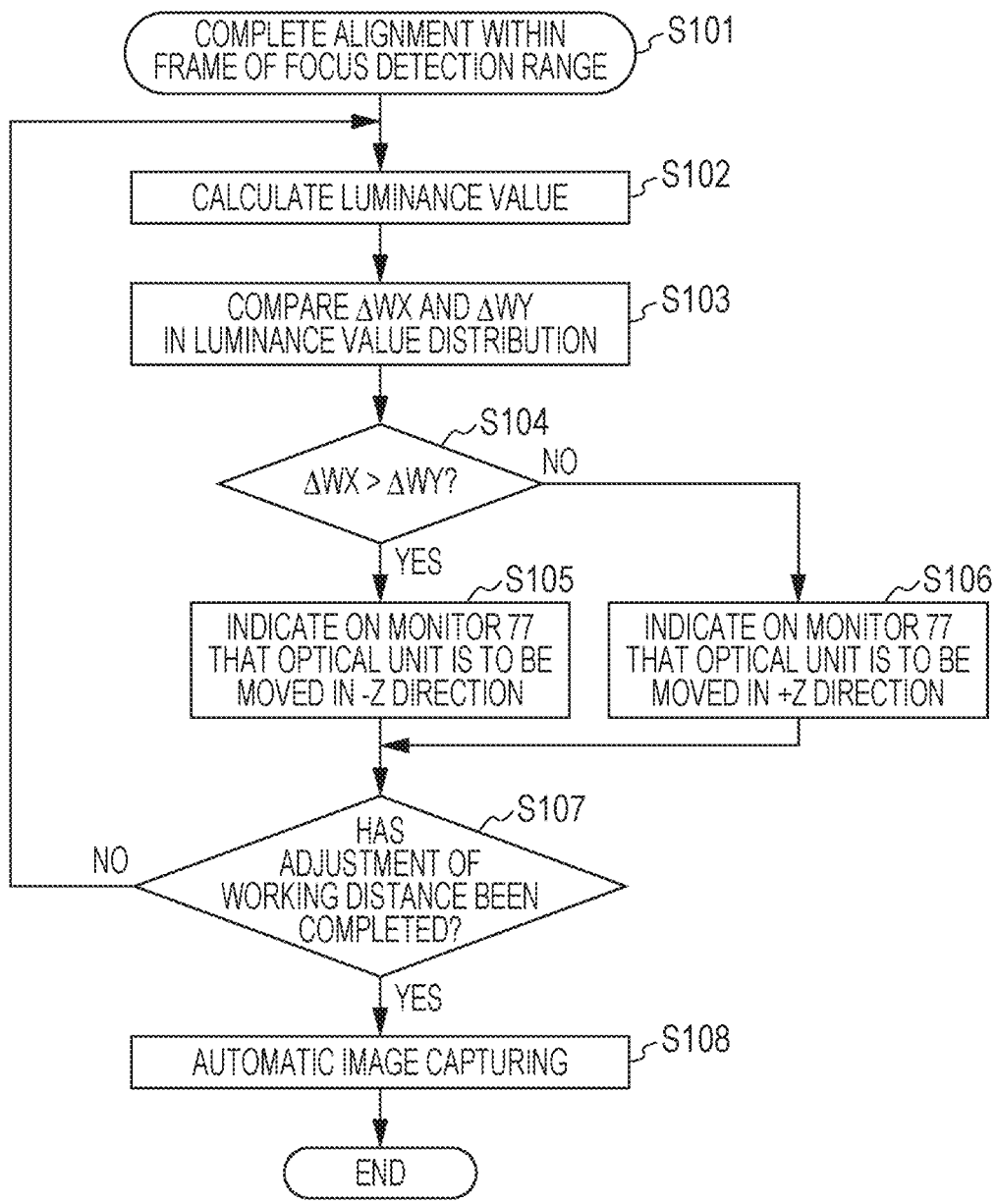
FIG. 12 is a flowchart for describing the exemplary embodiment.

With reference to FIGS. 12 and 13, of operation sequences of the exemplary embodiment, processing covering from the adjustment of the working distance to automatic image capturing will be described. This processing is carried out after the cornea reflection images L1 and L2 from the eye 28 are aligned within the frames of the focus detection ranges 77b and 77c, respectively.

First, a case in which the examiner manually moves the fundus camera optical unit 79 will be described with reference to FIG. 12. FIG. 12 is a flowchart illustrating the processing covering from the adjustment of the working distance to the automatic image capturing, of the operation sequences of the exemplary embodiment.

In step S101, the examiner completes the alignment of the cornea reflection images L1 and L2 from the eye 28 to fit within the frames of the focus detection ranges 77b and 77c, respectively, and the CPU 61 then starts the processing for adjusting the working distance.

In step S102, the focus evaluation value storage unit 71b calculates the luminance value distributions of the cornea reflection images L1 and L2 from the eye 28.

In step S103, the focus evaluation value storage unit 71b calculates $\Delta WX$ and $\Delta WY$ of the luminance value distributions.

In step S104, the focus evaluation value storage unit 71b compares $\Delta WX$ and $\Delta WY$. If $\Delta WX$ is greater than $\Delta WY$, the processing proceeds to step S105, or if $\Delta WX$ is smaller than $\Delta WY$, the processing proceeds to step S106.

In step S105, the CPU 61 displays, on the monitor 77, an indication that the fundus camera optical unit 79 is to be moved in the −Z direction. Thus, the examiner is prompted to move the fundus camera optical unit 79 in the −Z direction in order to bring the working distance to the appropriate distance.

In step S106, the CPU 61 displays, on the monitor 77, an indication that the fundus camera optical unit 79 is to be moved in the +Z direction. Thus, the examiner is prompted to move the fundus camera optical unit 79 in the +Z direction in order to bring the working distance to the appropriate distance.

In step S107, the CPU 61 determines whether the examiner has completed the adjustment of the working distance of the fundus camera optical unit 79 in the optical axis direction. If the CPU 61 determines that the examiner has not completed the adjustment of the working distance, the processing returns to step S102. If the CPU 61 determines that the examiner has completed the adjustment of the working distance, the processing proceeds to step S108.

In step S108, the CPU 61 executes the automatic image capturing. Specifically, the CPU 61 causes the imaging light source 13 to emit light through the imaging light source control circuit 62 and obtains a fundus image of the eye 28 with the image sensor element 31.

Thus far, the flowchart illustrated in FIG. 12 has been described.

Subsequently, processing in a configuration in which the fundus camera optical unit 79 automatically adjusts the working distance will be described with reference to FIG. 13. FIG. 13 is a flowchart illustrating the processing covering from the adjustment of the working distance to the automatic image capturing, of the operation sequences of the exemplary embodiment.

In step S201, the CPU 61 completes the alignment of the cornea reflection images L1 and L2 from the eye 28 to fit within the frames of the focus detection ranges 77b and 77c, respectively. Specifically, the CPU 61 instructs the M10 driving circuit 85 and the M11 driving circuit 86 to drive the X driving motor M10 and the Y driving motor M11, respectively, based on the outputs of the X position sensor 88 and the Y position sensor 89. Through this, the alignment is carried out to allow the cornea reflection images L1 and L2 from the eye 28 to fit within the frames of the focus detection ranges 77b and 77c, respectively.

Processes in steps S202 to S204 are the same as those in steps S102 to S104 described above, and thus descriptions thereof will be omitted. If it is determined in step S204 that $\Delta WX$ is greater than $\Delta WY$, the processing proceeds to step S205, or if it is determined that $\Delta WX$ is smaller than $\Delta WY$, the processing proceeds to step S206.

In step S205, the CPU 61 instructs the M12 driving circuit 87 to move the fundus camera optical unit 79 in the −Z direction. The M12 driving circuit 87 drives the Z driving motor M12 so as to move the fundus camera optical unit 79 in the −Z direction.

In step S206, the CPU 61 instructs the M12 driving circuit 87 to move the fundus camera optical unit 79 in the +Z direction. The M12 driving circuit 87 drives the Z driving motor M12 so as to move the fundus camera optical unit 79 in the +Z direction.

In step S207, the CPU 61 determines whether the adjustment of the working distance of the fundus camera optical unit 79 in the optical axis direction has been completed. If the working distance between the eye 28 and the fundus camera optical unit 79 has been brought to the appropriate distance (i.e., within an appropriate range), the CPU 61 determines that the adjustment of the working distance has been completed. If the CPU 61 determines that the adjustment of the working distance has not been completed, the processing returns to step S202. If the CPU 61 determines that the adjustment of the working distance has been completed, the processing proceeds to step S208.

A process in step S208 is the same as that in step S108 described above, and thus descriptions thereof will be omitted. Thus far, the flowchart illustrated in FIG. 13 has been described.

Note that, in the configuration in which the fundus camera optical unit 79 automatically adjusts the working distance, in steps S205 and S206, the direction in which the fundus camera optical unit 79 is to be moved may be displayed on the monitor 77.

According to the exemplary embodiment, the examiner can be notified of the direction in which the fundus camera optical unit 79 is to be moved in order to adjust the working distance. In addition, in the configuration in which the fundus camera optical unit 79 is moved automatically, the fundus camera optical unit 79 can be moved after the direction in which the fundus camera optical unit 79 is to be moved in order to adjust the working distance is determined. Accordingly, the working distance between the eye 28 and the fundus camera optical unit 79 can be adjusted promptly.

Other Embodiments

Additional embodiments can also be realized by a computer of a system or apparatus that reads out and executes computer executable instructions recorded on a storage medium (e.g., computer-readable storage medium) to perform the functions of one or more of the above-described embodiment(s), and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

Although an example in which the present disclosure is applied to the fundus camera has been described in the exemplary embodiment above, this embodiment is not limited to be limiting and can be applied to any ophthalmologic apparatus. In other words, various types of ophthalmologic photographing apparatuses and ocular refractivity measurement apparatuses are applicable.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-083947, filed Apr. 12, 2013, which is hereby incorporated by reference herein in its entirety.

What is claimed is:

1. An ophthalmologic apparatus, comprising:
   an optical unit configured to capture an image of an eye to be examined;
   a target projection unit configured to project a target on the eye to be examined, the target being used to adjust a working distance between the eye to be examined and the optical unit; and
   a determination unit configured to determine whether the working distance is appropriate based on a cornea reflection image from the eye to be examined, the cornea reflection image being captured by the optical unit,
   wherein the determination unit determines a moving direction of the optical unit in which the working distance is appropriate based on a direction of a blur due to an influence of astigmatism contained in the cornea reflection image captured by the optical unit.

2. The ophthalmologic apparatus according to claim 1, wherein the determination unit determines that the working distance is not appropriate in a case where a blur in the cornea reflection image in a first direction is larger than a blur in the cornea reflection image in a second direction different from the first direction.

3. The ophthalmologic apparatus according to claim 1, further comprising:
   a notification unit configured to provide a notification of the moving direction of the optical unit in which the working distance is appropriate determined by the determination unit.

4. The ophthalmologic apparatus according to claim 1, further comprising:
   a driving unit configured to move the optical unit in the direction in which the working distance is appropriate determined by the determination unit.

5. The ophthalmologic apparatus according to claim 1, wherein the determination unit is configured to determine the moving direction of the optical unit in which the moving distance is appropriate based on a direction in which a blur in the cornea reflection image is larger of a first direction and a second direction different from the first direction.

6. The ophthalmologic apparatus according to claim 5, wherein the first direction is perpendicular to the second direction.

7. The ophthalmologic apparatus according to claim 6, wherein the determination unit is configured
   to determine that the moving direction of the optical unit in which the working distance is appropriate, in a case where the blur in the cornea reflection image in the first direction is larger than the blur in the cornea reflection image in the second direction, is a direction in which the optical unit is moved away from the eye to be examined, and
   to determine that the moving direction of the optical unit in which the working distance is appropriate, in a case where the blur in the cornea reflection image in the second direction is larger than the blur in the cornea reflection image in the first direction, is a direction in which the optical unit is moved closer to the eye to be examined.

8. The ophthalmologic apparatus according to claim 5, wherein the determination unit is configured to determine the direction in which the blur in the cornea reflection image is larger of the first direction and the second direction different from the first direction by comparing a luminance value distribution of the cornea reflection image along the first direction with a luminance value distribution of the cornea reflection image along the second direction.

9. The ophthalmologic apparatus according to claim 6, wherein the determination unit is configured to determine the direction in which the blur in the cornea reflection image is larger of the first direction and the second direction by comparing a luminance value distribution of the cornea reflection image along the first direction with a luminance value distribution of the cornea reflection image along the second direction.

10. The ophthalmologic apparatus according to claim 1, further comprising:
    an imaging unit configured to capture the cornea reflection image and a fundus image of the eye to be examined; and
    a lens driving unit configured to move the focus lens based on the fundus image.

11. The ophthalmologic apparatus according to claim 10, further comprising:
    a display control unit configured to cause a display unit to display the fundus image of the eye to be examined and the cornea reflection image,
    wherein the lens driving unit is configured to move the focus lens based on a part of the fundus image, and
    wherein the display control unit is configured to cause the display unit to display, on the fundus image, a frame indicating the part of the fundus image and a frame indicating an appropriate position of the cornea reflection image.

12. The ophthalmologic apparatus according to claim 1, further comprising:
    a display control unit configured to cause a display unit to display a fundus image of the eye to be examined and the cornea reflection image and a frame indicating an appropriate position of the cornea reflection image, wherein the determination unit is configured to perform determination after the cornea reflection image is positioned within the frame.

13. The ophthalmologic apparatus according to claim 1, further comprising:
   an imaging unit configured to capture the cornea reflection image and a fundus image of the eye to be examined; and
   a display control unit configured to cause a display unit to display the cornea reflection image and the fundus image of the eye to be examined.

14. The ophthalmologic apparatus according to claim 1, wherein the determination unit is configured to determine whether the working distance is appropriate based on a plurality of cornea reflection images.

* * * * *